United States Patent

Malfer et al.

[11] Patent Number: 5,106,975
[45] Date of Patent: Apr. 21, 1992

[54] HEXAHYDROPYRIMIDINE DERIVATIVES

[75] Inventors: Dennis J. Malfer, Crestwood, Mo.; John G. Bostick, Belleville, Ill.; Lawrence J. Cunningham, Kirkwood; J. Vincent Hanlon, St. Louis, both of Mo.

[73] Assignee: Ethyl Petroleum Additives, Inc., St. Louis, Mo.

[21] Appl. No.: 438,164

[22] Filed: Nov. 20, 1989

Related U.S. Application Data

[63] Continuation-in-part of Ser. No. 318,748, Mar. 2, 1989.

[51] Int. Cl.$^5$ .......................................... C07D 239/26
[52] U.S. Cl. .................................................. 544/335
[58] Field of Search ........................................ 544/335

[56] References Cited

U.S. PATENT DOCUMENTS 3,988,367  10/1976  Gaudette et al. ................. 544/335

OTHER PUBLICATIONS

Crook et al., Chemical Abstracts, vol. 83, entry 180306z (1975).
Billman et al., J. Med. Chem., vol. 9, pp. 347–351 (1966).
Billman et al., Chemical Abstracts, vol. 64, entry 17590b (1966).

*Primary Examiner*—John M. Ford
*Attorney, Agent, or Firm*—J. F. Sieberth; David E. LaRose

[57] ABSTRACT

When a phenol having substituents in at least the 2- and 4-positions but having a hydrogen atom in the 6-position, or a phenol having substituents in at least the 2- and 6-positions but having a hydrogen atom in the 4-position is reacted with formaldehyde and 1,3-propanediamine, a unique insertion-condensation reaction occurs whereby the product is a hexahydropyrimidine derivative which may be represented by the general formula

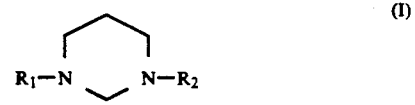

(I)

wherein $R_1$ is (i) a 2-hydroxybenzyl group having an inert substituent (preferably a hydrocarbyl substituent) in at least the 3- and 5-positions or (ii) a 4-hydroxybenzyl group having an inert substituent (preferably a hydrocarbyl substituent) in at least the 3- and 5-positions; and $R_2$ is (i) a 2-hydroxybenzyl group having an inert substituent (preferably a hydrocarbyl substituent) in at least the 3- and 5-positions or (ii) a 4-hydroxybenzyl group having an inert substituent (preferably a hydrocarbyl substituent) in at least the 3- and 5-positions or (iii) a hydrogen atom. Uses for such compounds include their use as antioxidants and stabilizers for various substrates, such as fuels, lubricants, and functional fluids.

49 Claims, No Drawings

HEXAHYDROPYRIMIDINE DERIVATIVES

REFERENCE TO RELATED APPLICATION

This application is a continuation-in-part of prior copending application Ser. No. 318,748, filed Mar. 2, 1989.

TECHNICAL FIELD AND BACKGROUND

This invention relates to novel chemical compounds which are formed by a highly unusual reaction mechanism. More particularly, this invention is directed to hexahydropyrimidine derivatives, the structure and formation of which could not have been (and in fact were not) anticipated or understood until the structural and mechanistic investigations by one of us (DJM).

In prior copending application Ser. No. 318,748, filed Mar. 2, 1989 by three of us (JGB, LJC and JVH), the use of certain additive mixtures as stabilizers for middle distillate fuels is set forth pursuant to the concept by such three of us. The additive mixtures of the prior application include a wide variety of Mannich bases. Included within the scope of the such Mannich bases is a new class of Mannich bases, the correct structural formula of which is set forth in the prior application. Such new Mannich bases fall within the scope of a larger class of novel compounds with which this application is concerned. The elucidation of the structures of these particular novel compounds resulted from the structural and mechanistic investigations by the other one of us (DJM).

The Mannich reaction among phenols, formaldehyde and amines is a well-known reaction which has been extensively documented in the literature. However, to the best of our knowledge and belief, the rearrangements and mechanistic aspects involved in the formation of the compounds of this invention are wholly unprecedented. In simple terms, given the identities of the reactants from which the compounds of this invention are made, the course of the reaction and the particular structural make-up of the products of such reaction could not have been predicted on the basis of pre-existing knowledge.

The Invention

In accordance with invention it has been discovered that when a phenol having substituents in at least the 2- and 4-positions but having a hydrogen atom in the 6-position, or a phenol having substituents in at least the 2- and 6-positions but having a hydrogen atom in the 4-position is reacted with formaldehyde and 1,3-propanediamine, a unique insertion-condensation reaction occurs whereby the product is a hexahydropyrimidine derivative which may be represented by the general formula

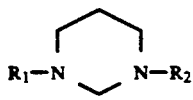

(I)

wherein $R_1$ is (i) a 2-hydroxybenzyl group having an inert substituent (preferably a hydrocarbyl substituent) in at least the 3- and 5-positions or (ii) a 4-hydroxybenzyl group having an inert substituent (preferably a hydrocarbyl substituent) in at least the 3- and 5-positions; and $R_2$ is (i) a 2-hydroxybenzyl group having an inert substituent (preferably a hydrocarbyl substituent) in at least the 3- and 5-positions or (ii) a 4-hydroxybenzyl group having an inert substituent (preferably a hydrocarbyl substituent) in at least the 3- and 5-positions or (iii) a hydrogen atom.

This invention thus provides the novel and useful compounds of formula (I) above. In addition this invention provides a process of producing the compounds of formula (I) above which comprises reacting formaldehyde and 1,3-propanediamine with (i) at least one phenol having a hydrogen atom in the 6-position and having an inert substituent (preferably a hydrocarbyl substituent) in at least the 2- and 4-positions, or (ii) at least one phenol having a hydrogen atom in the 4-position and having an inert substituent (preferably a hydrocarbyl substituent) in at least the 2- and 6-positions, or (iii) a mixture of at least one phenol having a hydrogen atom in the 6-position and having an inert substituent (preferably a hydrocarbyl substituent) in at least the 2- and 4-positions and at least one phenol having a hydrogen atom in the 4-position and having an inert substituent (preferably a hydrocarbyl substituent) in at least the 2- and 6-positions. In all such cases the 3- and/or 5-position(s) of the 2,4- and/or 2,6-substituted phenolic reactant(s) can be substituted with an inert substituent. In this specification in the appended claims the term "inert" is used in the sense that the substituent does not interfere with the reaction or otherwise prevent the formation of a compound or a mixture of compounds of formula (I)—the substituent is, in other words, an innocuous substituent as it does no material harm either to the reaction or to the desired product(s) of the reaction. Examples of such inert substituents include hydrocarbyl and hydrocarbyloxy groups such as alkyl, alkenyl, cycloalkyl, cycloalkylalkyl, aryl, aralkyl, alkoxy, cycloalkyloxy, aryloxy, alkoxyalkyl, etc., with the proviso that their location, size and configuration are such as not to sterically hinder the reactive (hydrogen atom-bearing) 4- or 6-position of the phenolic reactant(s); halogen atoms; haloaryl groups with the proviso that their location, size, composition, and configuration are such as not to sterically hinder the reactive 4- or 6-position of the phenolic reactant(s) or otherwise interfere with the formation and existance of the desired product(s); hydroxyl; carboxyl; nitro; dihydrocarbylamino; and the like.

There are five individual subgroups of compounds provided by this invention, viz. compounds of formula (I) above:

1) wherein $R_1$ is a 2-hydroxybenzyl group having an inert substituent (preferably a hydrocarbyl substituent) in at least the 3- and 5-positions, and $R_2$ is a hydrogen atom;

2) wherein $R_1$ is a 4-hydroxybenzyl group having an inert substituent (preferably a hydrocarbyl substituent) in at least the 3- and 5-positions, and $R_2$ is a hydrogen atom;

3) wherein $R_1$ is a 2-hydroxybenzyl group having an inert substituent (preferably a hydrocarbyl substituent) in at least the 3- and 5-positions, and $R_2$ is also a 2-hydroxybenzyl group having an inert substituent (preferably a hydrocarbyl substituent) in at least the 3- and 5-positions;

4) wherein $R_1$ is a 4-hydroxybenzyl group having an inert substituent (preferably a hydrocarbyl substituent) in at least the 3- and 5-positions, and $R_2$ is also a 4-hydroxybenzyl group having an inert substituent (preferably a hydrocarbyl substituent) in at least the 3- and 5-positions; and 5) wherein $R_1$ is a 2-hydroxybenzyl group having an inert substituent (preferably a hydrocarbyl substituent) in at least the 3- and 5-positions, and $R_2$ is a 4-hydroxybenzyl group having an inert substituent (preferably a hydrocarbyl substituent) in at least the 3- and 5-positions.

In categories 3) and 4) above, the two hydroxybenzyl groups may contain the same or different substituents; preferably however, the two hydroxybenzyl groups are the same. To illustrate, a category 4) compound of this invention in which the 4-hydroxybenzyl groups contain different substituents is N-(4-hydroxy-3,5-di-tert-butylbenzyl)-N'-(4-hydroxy-3-methyl-5-tertbutylbenzyl)hexahydropyrimidine, a compound of formula I above in which $R_1$ is a 4-hydroxy-3,5-tert-butylbenzyl group and $R_2$ is a 4-hydroxy-3-methyl-5-tert-butylbenzyl group. An example of a compound in which $R_1$ and $R_2$ are the same (and thus such compound is representative of a more preferred compound of this invention) is N,N'-bis(4-hydroxy-3,5-di-tert-butylbenzyl)hexahydropyrimidine, a compound which according to current preferred nomenclature can also be named 4,4'-[1,3-hexahydropyrimidinediylbis(methylene)]bis(2,6-di-tertbutylphenol). The purist might prefer to identify the tert-butyl group as the 1,1-dimethylethyl group, but in the interest of brevity and simplicity the term "tertbutyl" is used herein. Likewise, in the interests of consistency and clarity in naming monohydric compounds of this invention using such preferred nomenclature, the compounds will be named herein as a "phenol" even though in some cases they could be named as a "cresol" or a "xylenol", etc. Also, the 2-(1,3-hexahydropyrimidine) substituent group(s) and/or 4-(1,3-hexahydropyrimidine) substituent group(s) will be referred to first, followed by the remaining substituents of the phenol in numerical order; the rule of identifying substituents in alphabetical order will not be followed herein. Asymmetrical compounds are named by use of IUC-type nomenclature.

Particularly preferred compounds of this invention are compounds of formula (I) above falling within category 2) wherein $R_1$ is a 4-hydroxybenzyl group having a hydrocarbyl substituent in at least the 3- and 5-positions, and $R_2$ is a hydrogen atom; or within category 4) wherein each of $R_1$ and $R_2$ is a 4-hydroxybenzyl group having a hydrocarbyl substituent in at least the 3-and 5-positions, especially where the two substituted 4-hydroxybenzyl groups are identical to each other.

Also provided by this invention are mixtures of compounds from two or more of categories 1), 2), 3), 4), and 5), such as the binary mixtures composed of:

at least one compound from 1) and at least one compound from 2);

at least one compound from 1) and at least one compound from 3);

at least one compound from 1) and at least one compound from 4);

at least one compound from 1) and at least one compound from 5);

at least one compound from 2) and at least one compound from 3);

at least one compound from 2) and at least one compound from 4);

at least one compound from 2) and at least one compound from 5);

at least one compound from 3) and at least one compound from 4);

at least one compound from 3) and at least one compound from 5);

at least one compound from 4) and at least one compound from 5);

as well as the various ternary and quaternary mixtures, such as:

at least one compound from 1), at least one compound from 2), and at least one compound from 3);

at least one compound from 1), at least one compound from 2), and at least one compound from 4);

at least one compound from 1), at least one compound from 2), and at least one compound from 5);

at least one compound from 1), at least one compound from 3), and at least one compound from 4);

at least one compound from 1), at least one compound from 3), and at least one compound from 5);

at least one compound from 1), at least one compound from 4), and at least one compound from 5);

at least one compound from 2), at least one compound from 3), and at least one compound from 4);

at least one compound from 2), at least one compound from 3), and at least one compound from 5);

at least one compound from 2), at least one compound from 4), and at least one compound from 5);

at least one compound from 3), at least one compound from 4), and at least one compound from 5);

at least one compound from 1), at least one compound from 2), at least one compound from 3), and at least one compound from 4);

at least one compound from 1), at least one compound from 2), at least one compound from 3), and at least one compound from 5);

at least one compound from 1), at least one compound from 2), at least one compound from 4), and at least one compound from 5);

at least one compound from 1), at least one compound from 3), at least one compound from 4), and at least one compound from 5); and at least one compound from 2), at least one compound from 3), at least one compound from 4), and at least one compound from 5).

The five-component mixtures—i.e., at least one compound from 1), at least one compound from 2), at least one compound from 3), at least one compound from 4); and at least one compound from 5)—are also within the ambit of this invention.

The preferred mixtures are the binary systems composed predominantly or entirely of at least one compound from 1) and at least one compound from 3); and even more preferably, at least one compound from 2) and at least one compound from 4), especially where the two substituted 4-hydroxybenzyl groups are identical to each other and the substituents on both such groups are hydrocarbyl substituents.

The above and still other embodiments and features of this invention will be apparent from a consideration of the ensuing description and appended claims.

DETAILED DESCRIPTION

To a large extent the proportions of the reactants used in the process govern the product distribution in the reaction product. For example, formation of a product enriched in compound(s) of category 1) above with little or no compound(s) of category 3) above, or alternatively, a product enriched in compound(s) of category 2) above with little or no compound(s) of category 4) above is favored when using mole ratios of the phenolic reactant(s):formaldehyde:1,3-propanediamine in the range of about 1:2:1 to about 1:2:2, respectively. Conversely, formation of a product enriched in compound(s) of category 3) above with little or no compound(s) of category 1) above or alternatively, a product enriched in compound(s) of category 4) above with little or no compound(s) of category 1) above is favored when using mole ratios of phenolic reactant(s):formaldehyde:1,3-propanediamine in the range of about 2:3:1 to about 2:4:1, respectively. Products enriched in compounds of category 5) above result when employing a suitable mixture of phenol(s) having a hydrogen atom in the 6-position and substituted at least in the 2- and 4-positions and phenol(s) having a hydrogen atom in the 4-position and substituted at least in the 2- and 6-positions (e.g., a mixture of 2,4-dialkylphenol(s) and 2,6-dialkylphenol(s) in a mole ratio of 40:60 to 60:40, preferably in essentially equimolar amounts) with formaldehyde and 1,3-propanediamine in mole ratios (phenols:formaldehyde:1,3-propanediamine) in the range of about 2:3:1 to about 2:4:1, respectively. It is to be noted that such phenol(s) substituted at least in the 2- and 4-positions and such phenol(s) substituted at least in the 2- and 6-positions need not be used in mixed form —a suitable quantity of such phenol(s) substituted at least in the 2- and 4-positions can be reacted with the formaldehyde and 1,3-propanediamine and then a suitable quantity of such phenol(s) substituted at least in the 2- and 6-positions can be reacted with the product so formed, or these phenolic reactants may be reacted in the reverse order with the formaldehyde and 1,3-propanediamine. In short, the proper quantities of the phenolic reactants may be reacted concurrently or sequentially with the formaldehyde and 1,3-propanediamine in any order or sequence. When desired, the individual compounds of this invention may be isolated from product mixtures by fractional distillation at suitably reduced pressures, by solvent extraction procedures, by use of column chromatography, or by like methods of separation.

Although the process of this invention can be conducted in bulk (i.e., without use of an ancillary solvent or diluent), it is generally preferred to conduct the reaction in a suitable inert liquid reaction medium, such as in one or more alcohols, aliphatic hydrocarbons, cycloaliphatic hydrocarbons, aromatic hydrocarbons, halohydrocarbons, halocarbons, ethers, tertiary amines, siloxanes, silanes, etc., or mixtures of such solvent types. The process is normally conducted at a suitably elevated temperature, for example in the range of from about 50 to about 120° C., and preferably in the range of from about 80 to about 85° C. Ordinarily, ambient pressures are employed, although use of superatmospheric pressures may prove useful, especially when employing formaldehyde in its gaseous form. In this connection, the formaldehyde may be used in any suitable reactive form such as gaseous monomeric formaldehyde, lower reactive oligomeric forms of formaldehyde, and the like. The preferred forms of formaldehyde for use in the process of this invention are solutions of formaldehyde in lower alkanols such as methanol, ethanol, n-propanol, n-butanol, iso-butanol, etc. Formaldehyde-alkanol solutions of different concentrations, e.g., methanol solutions of up to about 55% formaldehyde, and solutions of up to about 40% formaldehyde in other alkanols are available as articles of commerce and are preferred for use in the process.

Methods for the production of phenols having inert substituent groups in at least the 2- and 4-positions but with a hydrogen atom in the 6-position and for the production of phenols having inert substituent groups in at least the 2- and 6-positions but with a hydrogen atom in the 4-position are known to those skilled in the art and are well documented in the literature. Moreover, a number of such compounds are available as articles of commerce from various suppliers. Consequently further description of such methods herein would be redundant.

Illustrative compounds of this invention include the following:

Category 1)

2-(1,3-hexahydropyrimidinylmethylene)-4,6-dimethylphenol;

2-(1,3-hexahydropyrimidinylmethylene)-4-methyl-6-tert-butylphenol;

2-(1,3-hexahydropyrimidinylmethylene)-4-methyl-6-isopropylphenol;

2-(1,3-hexahydropyrimidinylmethylene)-4,6-diisopropylphenol;

2-(1,3-hexahydropyrimidinylmethylene)-4,6-di-tert-butylphenol;

2-(1,3-hexahydropyrimidinylmethylene)-4-methyl-6-(1,1,2-trimethylpropyl)phenol;

2-(1,3-hexahydropyrimidinylmethylene)-4-methyl-6-(1,1,3,3-tetramethylbutyl)phenol;

2-(1,3-hexahydropyrimidinylmethylene)-4-tert-amyl-6-tert-butyl)-phenol;

2-(1,3-hexahydropyrimidinylmethylene)-4-nonyl-6-tert-butyl)phenol;

2-(1,3-hexahydropyrimidinylmethylene)-4,6-dichlorophenol;

2-(1,3-hexahydropyrimidinylmethylene)-4,6-dimethoxyphenol;

2-(1,3-hexahydropyrimidinylmethylene)-4,6-di-(trifluoromethyl)-phenol;

2-(1,3-hexahydropyrimidinylmethylene)-3,4,6-trimethylphenol;

2-(1,3-hexahydropyrimidinylmethylene)-4,6-diethylphenol;

2-(1,3-hexahydropyrimidinylmethylene)-4-ethyl-6-tert-butylphenol;

2-(1,3-hexahydropyrimidinylmethylene)-4-methoxy-6-tert-butylphenol 2-(1,3-hexahydropyrimidinylmethylene)-4-phenoxy-6-methylphenol;

2-(1,3-hexahydropyrimidinylmethylene)-4-phenoxy-6-tert-butylphenol 2-(1,3-hexahydropyrimidinylmethylene)-3,6-dimethyl-4-bromophenol;

2-(1,3-hexahydropyrimidinylmethylene)-4,6-dimethyl-5-chlorophenol;

2-(1,3-hexahydropyrimidinylmethylene)-3-chloro-4,6-dimethylphenol;

2-(1,3-hexahydropyrimidinylmethylene)-3-fluoro-4,6-di-tert-butylphenol;

2-(1,3-hexahydropyrimidinylmethylene)-3-chloro-4,6-dimethylphenol;

2-(1,3-hexahydropyrimidinylmethylene)-3-fluoro-4-butyl-6-methylphenol;

2-(1,3-hexahydropyrimidinylmethylene)-4-trifluoromethyl-6-methylphenol;

2-(1,3-hexahydropyrimidinylmethylene)-4-phenyl-6-tert-butylphenol;

2-(1,3-hexahydropyrimidinylmethylene)-4-benzyl-6-tert-butylphenol;
2-(1,3-hexahydropyrimidinylmethylene)-4,6-diethoxyphenol;
2-(1,3-hexahydropyrimidinylmethylene)-4,6-diphenoxylphenol;
and the like.

Category 2)

4-(1,3-hexahydropyrimidinylmethylene)-2,6-dimethylphenol;
4-(1,3-hexahydropyrimidinylmethylene)-2-methyl-6-tert-butylphenol;
4-(1,3-hexahydropyrimidinylmethylene)-2-methyl-6-isopropylphenol;
4-(1,3-hexahydropyrimidinylmethylene)-2,6-diisopropylphenol;
4-(1,3-hexahydropyrimidinylmethylene)-2,6-di-tert-butylphenol;
4-(1,3-hexahydropyrimidinylmethylene)-2-methyl-6-(1,1,2-trimethylpropyl)phenol;
4-(1,3-hexahydropyrimidinylmethylene)-2-methyl-6-(1,1,3,3-tetramethylbutyl)phenol;
4-(1,3-hexahydropyrimidinylmethylene)-2-methoxy-6-tert-butyl)-phenol;
4-(1,3-hexahydropyrimidinylmethylene)-2-chloro-6-tert-butyl)phenol;
4-(1,3-hexahydropyrimidinylmethylene)-2,6-dichlorophenol;
4-(1,3-hexahydropyrimidinylmethylene)-2,6-dimethoxyphenol;
4-(1,3-hexahydropyrimidinylmethylene)-2,6-di-(trifluoromethyl)-phenol;
4-(1,3-hexahydropyrimidinylmethylene)-2,3,6-trimethylphenol;
4-(1,3-hexahydropyrimidinylmethylene)-2,6-diethylphenol;
4-(1,3-hexahydropyrimidinylmethylene)-2-ethyl-6-tert-butylphenol;
4-(1,3-hexahydropyrimidinylmethylene)-2-fluoro-6-tert-butylphenol;
4-(1,3-hexahydropyrimidinylmethylene)-2-phenoxy-6-methylphenol;
4-(1,3-hexahydropyrimidinylmethylene)-2-phenoxy-6-tert-butylphenol;
4-(1,3-hexahydropyrimidinylmethylene)-2-bromo-3,6-dimethylphenol;
4-(1,3-hexahydropyrimidinylmethylene)-2,6-dimethyl-3-chlorophenol;
4-(1,3-hexahydropyrimidinylmethylene)-2,6-dimethyl-3-fluorophenol;
4-(1,3-hexahydropyrimidinylmethylene)-2,6-di-tert-butyl-3-fluorophenol;
4-(1,3-hexahydropyrimidinylmethylene)-2,6-diethyl-3-chlorophenol;
4-(1,3-hexahydropyrimidinylmethylene)-2-tert-butyl-3-fluoro-6-methylphenol;
4-(1,3-hexahydropyrimidinylmethylene)-2-trifluoromethyl-6-methylphenol;
4-(1,3-hexahydropyrimidinylmethylene)-2-phenyl-6-tert-butylphenol;
4-(1,3-hexahydropyrimidinylmethylene)-2-benzyl-6-tert-butylphenol;
4-(1,3-hexahydropyrimidinylmethylene)-2,6-diethoxyphenol;
4-(1,3-hexahydropyrimidinylmethylene)-2,6-diphenoxylphenol;
and the like.

Category 3)

2,2'-[1,3-hexahydropyrimidinediylbis(methylene)]-bis(4,6-dimethylphenol);
2,2'-[1,3-hexahydropyrimidinediylbis(methylene)]bis(4-methyl-6-isopropylphenol;
2,2'-[1,3-hexahydropyrimidinediylbis(methylene)]bis(4-methyl-6-tert-butylphenol;
2,2'-[1,3-hexahydropyrimidinediylbis(methylene)]-bis(4,6-diisopropylphenol;
2,2'-[1,3-hexahydropyrimidinediylbis(methylene)]-bis(4,6-di-tertbutylphenol;
2,2'-[1,3-hexahydropyrimidinediylbis(methylene)]bis(4-methyl-6-(1,1,2-trimethylpropyl)phenol;
2,2'-[1,3-hexahydropyrimidinediylbis(methylene)]bis(4-methyl-6-(1,1,3,3-tetramethylbutyll)phenol;
2,2'-[1,3-hexahydropyrimidinediylbis(methylene)]bis(4-tert-amyl-6-tert-butylphenol;
2,2'-[1,3-hexahydropyrimidinediylbis(methylene)]bis(4-nonyl-6-tertbutylphenol;
2,2'-[1,3-hexahydropyrimidinediylbis(methylene)]-bis(3,5,6-trimethylphenol);
2,2'-[1,3-hexahydropyrimidinediylbis(methylene)]-bis(4,5,6-trimethylphenol);
2,2'-[1,3-hexahydropyrimidinediylbis(methylene)]-bis(3,4,5,6-tetramethylphenol);
2,2'-[1,3-hexahydropyrimidinediylbis(methylene)]-bis(4,6-dichlorophenol);
2,2'-[1,3-hexahydropyrimidinediylbis(methylene)]-bis(4,6-dimethoxy=phenol);
2,2'-[1,3-hexahydropyrimidinediylbis(methylene)]bis(4-phenyl-6-methylphenol);
2,2'-[1,3-hexahydropyrimidinediylbis(methylene)]bis(4-phenoxy-6-methylphenol);
2,2'-[1,3-hexahydropyrimidinediylbis(methylene)]bis(3-fluoro-4,6-di-tert-butylphenol;
2,2'-[1,3-hexahydropyrimidinediylbis(methylene)]-bis(3,4,5,6-tetrachlorophenol);
2,2'-[1,3-hexahydropyrimidinediylbis(methylene)]bis(6-methoxyhydroquinone);
2,2'-[1,3-hexahydropyrimidinediylbis(methylene)]bis(6-fluorohydroquinone);
2,2'-[1,3-hexahydropyrimidinediylbis(methylene)]-bis(4,6-dichlororesorcinol);
2,2'-[1,3-hexahydropyrimidinediylbis(methylene)]bis(6-methoxyresorcinol);
2,2'-[1,3-hexahydropyrimidinediylbis(methylene)]bis(4-methoxy-6-tert-butylphenol);
2,2'-[1,3-hexahydropyrimidinediylbis(methylene)]bis(4-allyl-6-methoxyphenol);
N-(2-hydroxy-3,5-dimethylbenzyl)-N-(2-hydroxy-3,5-di-tert-butylbenzyl)-1,3-hexahydropyrimidine;
and the like.

Category 4)

4,4'-[1,3-hexahydropyrimidinediylbis(methylene)]-bis(2,6-dimethylphenol);
4,4'-[1,3-hexahydropyrimidinediylbis(methylene)]bis(2-methyl-6-isopropylphenol;
4,4'-[1,3-hexahydropyrimidinediylbis(methylene)]-bis(2-methyl-6-tert-butylphenol;
4,4'-[1,3-hexahydropyrimidinediylbis(methylene)]-bis(2,6-diisopropylphenol);
4,4'-[1,3-hexahydropyrimidinediylbis(methylene)]-bis(2,6-di-tertbutylphenol);
4,4'-[1,3-hexahydropyrimidinediylbis(methylene)]bis(2-methyl-6-(1,1,2-trimethylpropyl)phenol;

4,4'-[1,3-hexahydropyrimidinediylbis(methylene)]bis(2-methyl-6-(1,1,3,3-tetramethylbutyll)phenol;
4,4'-[1,3-hexahydropyrimidinediylbis(methylene)]bis(2-chloro-6-tert-butylphenol;
4,4'-[1,3-hexahydropyrimidinediylbis(methylene)]bis(2-methoxy-6-tert-butylphenol;
4,4'-[1,3-hexahydropyrimidinediylbis(methylene)]-bis(2,3,6-trimethylphenol);
4,4'-[1,3-hexahydropyrimidinediylbis(methylene)]-bis(2,6-dinitrophenol);
4,4'-[1,3-hexahydropyrimidinediylbis(methylene)]-bis(2,3,5,6-tetramethylphenol);
4,4'-[1,3-hexahydropyrimidinediylbis(methylene)]-bis(2,6-dichlorophenol);
4,4'-[1,3-hexahydropyrimidinediylbis(methylene)]-bis(2,6-dimethoxyphenol);
4,4'-[1,3-hexahydropyrimidinediylbis(methylene)]bis(2-phenyl-6-methylphenol);
4,4'-[1,3-hexahydropyrimidinediylbis(methylene)]bis(2-phenoxy-6-methylphenol);
4,4'-[1,3-hexahydropyrimidinediylbis(methylene)]-bis(2,6-di-tertbutyl-3-fluorophenol;
4,4'-[1,3-hexahydropyrimidinediylbis(methylene)]-bis(2,3,5,6-tetrachlorophenol);
4,4'-[1,3-hexahydropyrimidinediylbis(methylene)]bis(6-methoxycatechol);
4,4'-[1,3-hexahydropyrimidinediylbis(methylene)]bis(6-fluorocatechol);
4,4'-[1,3-hexahydropyrimidinediylbis(methylene)]-bis(2,6-dichlororesorcinol);
4,4'-[1,3-hexahydropyrimidinediylbis(methylene)]bis(6-methoxyresorcinol);
4,4'-[1,3-hexahydropyrimidinediylbis(methylene)]-bis(2,3-dimethoxy-6-tert-butylphenol);
4,4'-[1,3-hexahydropyrimidinediylbis(methylene)]bis(2-cyclohexyl-6-methylphenol);
N-(4-hydroxy-3,5-dimethylbenzyl)-N'-(4-hydroxy-3,5-di-tert-butyl benzyl)-1,3-hexahydropyrimidine;
N-(4-hydroxy-3-methyl-5-tert-butylbenzyl)-N'-(4-hydroxy-3,5-ditert-butylbenzyl)-1,3-hexahydropyrimide;
and the like.

Category 5)

N-(4-hydroxy-3,5-dimethylbenzyl)-N'-(2-hydroxy-3,5-dimethylbenzyl)-1,3-hexahydropyrimidine;
N-(4-hydroxy-3,5-diisopropylbenzyl)-N'-(2-hydroxy-3,5-diisopropylbenzyl)-1,3-hexahydropyrimidine;
N-(4-hydroxy-3,5-di-tert-butylbenzyl)-N'-(2-hydroxy-3,5-di-tertbutylbenzyl)-1,3-hexahydropyrimidine;
N-(4-hydroxy-3-methyl-5-tert-butylbenzyl)-N'-(2-hydroxy-3-tertbutyl-5-methylbenzyl)-1,3-hexahydropyrimidine;
N-(4-hydroxy-3,5-dimethylbenzyl)-N'-(2-hydroxy-3,5-diisopropylbenzyl)-1,3-hexahydropyrimidine;
N-(4-hydroxy-3,5-dichlorobenzyl)-N'-(2-hydroxy-3,5-dichlorobenzyl)-1,3-hexahydropyrimidine;
N-(4-hydroxy-3,5-difluorobenzyl)-N'-(2-hydroxy-3,5-difluorobenzyl)-1,3-hexahydropyrimidine;
N-(4-hydroxy-3,5-dimethylbenzyl)-N'-(2-hydroxy-3,5-dichlorobenzyl)-1,3-hexahydropyrimidine;
N-(4-hydroxy-3,5-di-tert-butylbenzyl)-N'-(2-hydroxy-3-methoxy-5-allylbenzyl)-1,3-hexahydropyrimidine;
and the like.

The compounds of this invention are useful stabilizers and antioxidants for fuels, lubricants, and functional fluids such as gasoline, middle distillate fuels (e.g., diesel fuels, kerosene, jet fuels, burner fuels, gas turbine fuels, etc.), crankcase lubricating oils, automatic transmission fluids, gear oils, hydraulic fluids, and the like. A feature of these compounds is that the asymmetry of the 1,3-hexahydropyrimidine moiety generally enhances the solubility of the compounds in such substrates as compared to the solubility of a corresponding compound having a 1,4-piperazine moiety. The compounds having halogen or halogen-containing substituents are also useful as extreme pressure additives for lubricating oils, gear oils, cutting fluids, greases, and the like. In addition, the compounds of this invention can be used as stabilizers in condensation polymers, such as polyethylenes, polypropylenes, polybutenes, nylons, polyphenylene oxides, polyesters, and the like.

This invention will be still further apparent from the following illustrative examples of its practice and advantages. The examples are not intended to constitute, nor should they be construed as constituting, a limitation on this invention.

EXAMPLE 1

4,4'-[1,3-hexahydropyrimidinediylbis(methylene)]-bis(2,6-di-tert-butylphenol)

To a 500 mL flask add 206 g (1 mol) of 2,6-di-tert-butylphenol, 325 mL of isopropanol, and 37 g (0.5 mol) of 1,3-propanediamine. To this mixture, add 122 g (1.5 mols) of 37% formaldehyde. Warm the mixture to reflux and continue to reflux for approximately 4.5 hours (monitored by liquid chromatography). Set for distillation and remove most of the isopropanol. Usually 75-80% of the isopropanol can be removed before the solid gets too thick. Add 175 mL of heptane to the mixture and azeotrope the final amount of water. Cool the mixture and recrystallize from the heptane mixture to give 186 g (71%) of 4,4-[1,3-hexahydropyrmidinediylbis(methylene)]bis(2,6-di-tert-butylphenol):mp 115°–117° C.; $^{13}C[^1H]$ NMR (75.6 MHz, $CDCl_3$):22.7 ($CH_2$), 30.344 (tertiary carbon), [34.216,51.861, 59.595, 75.743] 125.8 (meta), 1.28.778 (para), 1.35.399 (ortho), 152.64 (phenol carbon); Chemical ionization exact mass Calc. for $C_{34}H_{54}N_2O_3$, (M+1), m/e 522.8217, found 522.4183. Anal. Calcd for $C_{34}H_{54}N_2O_2$:C, 74.95; H, 10.58; N, 9.2. Found:C, 74.99; H, 10.42; N, 9.16.

EXAMPLE 2

4-(1,3-hexahydropyrimidinylmethylene)-2,6-di-tert-butylphenol

To a 500 mL flask add 51.3 g (0.25 mols) of 2,6-di-tertbutylphenol, 120 mL of isopropanol, and 18.68 g (0.25 mols) of 1,3-propanediamine. To this mixture, slowly add 42.5 g (0.52 mols) of 37% formaldehyde. Warm the resulting mixture to reflux and reflux for approximately 4 hours (monitored by liquid chromatography). Set for distillation and remove most of the isopropanol. Usually 75% of the isopropanol can be removed before the solid gets too thick. To this mixture add 150 mL of heptane and azeotrope any excess water present. Cool the mixture and recrystallize from the heptane mixture to give 33.85 g (45%) of 4-(1,3-hexahydropyrmidinylmethylene)-2,6-di-tert-butylphenol:mp 135°–137° C.; $^{13}C[^1H]$ NMR (75.6 MHz, $CDCl_3$):27.1 ($CH_2$), 30.26 ($CH_3$), 34.17 (tertiary carbon), [45.2, 52.85, 60.233, 69.625] $CH_2$, 125.66 (meta), 128.2, 135.55 (ortho), 152.646 (phenol carbon); mass spectrum (EIMS) m/e (percent relative abundance), 304($M^+$, 24.59), 303(45.59), 260 (25.72), 234 (23.56), 219 (67.63), 85 (100).

Chemical ionization exact mass Calc. for $C_{19}H_{32}N_2O$, (M+1), m/e 304.445, found 304.2512. Anal. Calcd for $C_{19}H_{32}N_2O$: C, 74.95; H, 10.58; N, 9.2. Found:C, 74.99; H, 10.42; N, 9.16.

EXAMPLE 3

4,4-[1,3-hexahydropyrimidinediylbis(methylene)]-bis(2,6-di-tert-butylphenol) and
4-(1,3-hexahydropyrimidinylmethylene)-2,6-ditert-butylphenol Dissolve 103 g (0.5 mol) of 2,6-di-tert-butylphenol in 100 g of isopropanol in a 500 mL round bottom flask. Add 18.5 g (0.25 mol) of 1,3-propanediamine dropwise over 15 minutes while the contents of the flask are stirred. There is an exotherm observed as the amine is added. Cool the contents of the flask to below 30° C. and add a 10% excess (44.6 g, −0.55 mol) of 37% aqueous formaldehyde solution dropwise over 30 minutes while maintaining the temperature below 30° C. Heat the contents of the flask to reflux and continue to reflux for one hour. Switch from reflux to distillation and distill off isopropanol to 105° C. Apply 28 in. Hg vacuum to remove residual materials. The total product yield is 122.2 or 96% of theory which contains both 4,4'-[1,3-hexahydropyrimidinediylbis(methylene)]-bis(2,6-di-tert-butylphenol) and 4-(1,3-hexahydropyrimidinylmethylene)-2,6-ditert-butylphenol.

EXAMPLE 4

4,4'-[1,3-hexahydropyrimidinediylbis(methylene)]-bis(2-methyl-6-tert-butylphenol)

Repetition of the procedure of Example 1 but substituting an equivalent amount of 2-methyl-6-tert-butylphenol for the 2,6-di-tert-butylphenol results in the formation of 4,4'-[1,3-hexahydropyrimidinediylbis(methylene)]bis(2-methyl-6-tert-butylphenol).

EXAMPLE 5

4-(1,3-hexahydropyrimidinylmethylene)-2-methyl-6-tert-butylphenol

Repetition of the procedure of Example 2 but substituting an equivalent amount of 2-methyl-6-tert-butylphenol for the 2,6-di-tert-butylphenol results in the formation of 4-(1,3-hexahydropyrimidinylmethylene)-2-methyl-6-tert-butylphenol.

EXAMPLE 6

4,4'-[1,3-hexahydropyrimidinediylbis(methylene)]-bis(2,6-diisooropylphenol)

Repetition of the procedure of Example 1 but substituting an equivalent amount of 2,6-diisopropylphenol for the 2,6-ditert-butylphenol results in the formation of 4,4'-[1,3-hexahydropyrimidinediylbis(methylene)]-bis(2,6-diisopropylphenol).

EXAMPLE 7

4-(1,3-hexahydropyrimidinylmethylene)-2,6-diisopropylphenol

Repetition of the procedure of Example 2 but substituting an equivalent amount of 2,6-diisopropylphenol for the 2,6-ditert-butylphenol results in the formation of 4-(1,3-hexahydropyrimidinylmethylene)-2,6-diisopropylphenol.

EXAMPLE 8

2,2'-[1,3-hexahydropyrimidinediylbis(methylene)]-bis(4,6-di-tert-butylphenol)

Repetition of the procedure of Example 1 but substituting an equivalent amount of 2,4-di-tert-butylphenol for the 2,6-di-tert-butylphenol results in the formation of 2,2'-[1,3-hexahydropyrimidinediylbis(methylene)]-bis(4,6-di-tert-butylphenol).

EXAMPLE 9

2-(1,3-hexahydropyrimidinylmethylene)-4,6-di-tert-butylphenol

Repetition of the procedure of Example 2 but substituting an equivalent amount of 2,4-di-tert-butylphenol for the 2,6-di-tert-butylphenol results in the formation of 2-(1,3-hexahydropyrimidinylmethylene)-4,6-di-tert-butylphenol.

EXAMPLE 10

2,2'-[1,3-hexahydropyrimidinediylbis(methylene)]-bis(4-methyl-6-tert-butylphenol)

Repetition of the procedure of Example 1 but substituting an equivalent amount of 4-methyl-6-tert-butylphenol for the 2,6-di-tert-butylphenol results in the formation of 2,2'-[1,3-hexahydropyrimidinediylbis(methylene)]bis(4-methyl-6-tert-butylphenol.

EXAMPLE 11

2-(1,3-hexahydropyrimidinylmethylene)-4-methyl-6-tert-butylphenol

Repetition of the procedure of Example 2 but substituting an equivalent amount of 4-methyl-6-tert-butylphenol for the 2,6-di-tert-butylphenol results in the formation of 2-(1,3-hexahydropyrimidinylmethylene)-4-methyl-6-tert-butylphenol.

EXAMPLE 12

4,4'-[1,3-hexahydropyrimidinediylbis(methylene)]-bis(2,6-dichlorophenol)

Reaction among formaldehyde, 1,3-propanediamine and 2,6-dichlorophenol in the relative proportions as in Example 1 results in the formation of 4,4'-[1,3-hexahydropyrimidinediylbis(methylene)]bis(2,6-dichlorophenol).

EXAMPLE 13

4-(1,3-hexahydropyrimidinylmethylene)-2,6-dichlorophenol

Reaction among formaldehyde, 1,3-propanediamine and 2,6-dichlorophenol in the relative proportions as in Example 2 results in the formation of 4-(1,3-hexahydropyrimidinylmethylene)-6-dichlorophenol.

EXAMPLE 14

2,2'-[1,3-hexahydropyrimidinediylbis(methylene)]-bis(4-methoxy-6-tert-butylphenol)

Reaction among formaldehyde, 1,3-propanediamine and 4-methoxy-6-tert-butylphenol in the relative proportions as in Example 1 results in the formation of 2,2'-[1,3-hexahydropyrimidinediylbis(methylene)]-bis(4-methoxy-6-tert-butylphenol).

EXAMPLE 15

2-(1,3-hexahydropyrimidinylmethylene)-4-methoxy-6-tert-butylphenol

Reaction among formaldehyde, 1,3-propanediamine and -methoxy-6-tert-butylphenol in the relative proportions as in Example 2 results in the formation of 2-(1,3-hexahydropyrimidinylmethylene)-4-methoxy-6-tert-butylphenol.

As noted above, the compounds of this invention effectively inhibit oxidative degradation in motor fuels and in industrial and automotive lubricants and functional fluids. The amounts of the compounds of this invention employed in the materials to be stabilized are dependent both upon the nature of the material itself and the oxidative conditions to be encountered. Generally speaking, amounts in the range of about 0.0001 to about 5% by weight of the material to be protected are satisfactory. In some cases such as where the antioxidant is employed in an article normally subjected to severe oxidizing conditions, somewhat higher concentrations are useful.

Other conventional additives may be employed in the various substrates being protected by use of the compounds of this invention. Thus the lubricant and functional fluid compositions may contain antiwear and extreme pressure additives, antirust additives, detergents and dispersants, viscosity index improvers, and the like. Likewise the fuel compositions may contain induction system cleanliness agents, cold starting aids, octane improvers, cetane improvers, fuel blending components (e.g., methanol, ethanol, methyl-tert-butyl ether, etc.), dyes, antirust agents, detergents, and the like.

This invention is susceptible to considerable variation within the spirit and scope of the appended claims, the forms hereinbefore set forth constituting preferred embodiments thereof.

What is claimed is:

1. A hexahydropyrimidine compound represented by the formula

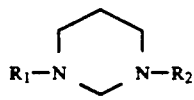

wherein $R_1$ is (i) a 2-hydroxybenzyl group having positions 3 and 5 wherein at least each of the 3 and 5 positions are substituted such that said substituted 3 and 5 positions do not interfere with the formation of said hexahydropyrimidine compound or (ii) a 4-hydroxybenzyl group having positions 3 and 5 wherein at least each of the 3 and 5 positions are substituted such that said substituted 3 and 5 positions do not interfere with the formation of said hexahydropyrimidine compound; and $R_2$ is (i) a 2-hydroxybenzyl group having positions 3 and 5 wherein at least each of the 3 and 5 positions are substituted such that said substituted 3 and 5 positions do not interfere with the formation of said hexahydropyrimidine compound or (ii) a 4-hydroxybenzyl group having positions 3 and 5 wherein at least each of the 3 and 5 positions are substituted such that said substituted 3 to 5 positions do not interfere with the formation of said hexahydropyrimidine compound or (iii) a hydrogen atom.

2. A compound of claim 1 wherein $R_2$ is a hydrogen atom.

3. A compound of claim 2 wherein $R_1$ is a 2-hydroxybenzyl group having a hydrocarbyl substituent in at least each of the 3 and 5 positions.

4. A compound of claim 3 wherein the 4 and 6 positions of the 2-hydroxybenzyl group both have a hydrogen atom thereon.

5. A compound of claim 3 wherein the hydrocarbyl substituents in the 3 and 5 positions of the 2-hydroxybenzyl group are alkyl groups.

6. A compound of claim 5 wherein at least one of said alkyl groups is a secondary or tertiary alkyl group.

7. A compound of claim 5 wherein both of said alkyl groups are secondary or tertiary alkyl groups.

8. A compound of claim 5 wherein one of said alkyl groups is a primary alkyl group and the other said alkyl group is a secondary or tertiary alkyl group.

9. A compound of claim 5 wherein one of said alkyl groups is a methyl group and the other said alkyl group is a tertiary alkyl group.

10. A compound of claim 9 wherein the tertiary alkyl group is a tertiary butyl group.

11. A compound of claim 5 wherein both of said alkyl groups are tertiary alkyl groups.

12. A compound of claim 11 wherein the tertiary alkyl groups are both tertiary butyl groups.

13. A compound of claim 2 wherein $R_1$ is a 4-hydroxybenzyl group having a hydrocarbyl substituent in at least each of the 3 and 5 positions.

14. A compound of claim 13 wherein the 2 and 6 positions of the 4-hydroxybenzyl group both have a hydrogen atom thereon.

15. A compound of claim 13 wherein the hydrocarbyl substituents in the 3 and 5 positions of the 4-hydroxybenzyl group are alkyl groups.

16. A compound of claim 15 wherein at least one of said alkyl groups is a secondary or tertiary alkyl group.

17. A compound of claim 15 wherein both of said alkyl groups are secondary or tertiary alkyl groups.

18. A compound of claim 15 wherein one of said alkyl groups is a primary alkyl group and the other said alkyl group is a secondary or tertiary alkyl group.

19. A compound of claim 15 wherein one of said alkyl groups is a methyl group and the other said alkyl group is a tertiary alkyl group.

20. A compound of claim 19 wherein the tertiary alkyl group is a tertiary butyl group.

21. A compound of claim 15 wherein both of said alkyl groups are tertiary butyl groups.

22. A compound of claim 21 wherein the tertiary alkyl groups are both tertiary butyl groups.

23. A compound of claim 1 wherein $R_2$ is other than a hydrogen atom.

24. A compound of claim 23 wherein $R_1$ and $R_2$ are the same and are both 2-hydroxybenzyl groups having a hydrocarbyl substituent in at least each of the 3 and 5 positions.

25. A compound of claim 24 wherein each of the 4 and 6 positions of the 2-hydroxybenzyl groups has a hydrogen atom thereon.

26. A compound of claim 24 wherein the hydrocarbyl substituents in the 3 and 5 positions of the 2-hydroxybenzyl groups are alkyl groups.

27. A compound of claim 26 wherein at least one of the alkyl groups in the 3 and 5 positions of the 2-hydroxybenzyl groups is a secondary or tertiary alkyl group.

28. A compound of claim 26 wherein both of the alkyl groups in the 3 and 5 positions of the 2-hydroxybenzyl groups are secondary or tertiary alkyl groups.

29. A compound of claim 26 wherein one of the alkyl groups in the 3 or 5 positions of the 2-hydroxybenzyl groups is a primary alkyl group and the other such alkyl group is a secondary or tertiary alkyl group.

30. A compound of claim 26 wherein one of the alkyl groups in the 3 or 5 positions of the 2-hydroxybenzyl groups is a methyl group and the other such alkyl group is a tertiary alkyl group.

31. A compound of claim 30 wherein the tertiary alkyl group is a tertiary butyl group.

32. A compound of claim 26 wherein both of the alkyl groups in the 3 and 5 positions of the 2-hydroxybenzyl groups are tertiary alkyl groups.

33. A compound of claim 32 wherein the tertiary alkyl groups are both tertiary butyl groups.

34. A compound of claim 23 wherein $R_1$ and $R_2$ are the same and are both 4-hydroxybenzyl groups having a hydrocarbyl substituent in at least each of the 3 and 5 positions thereof.

35. A compound of claim 34 wherein each of the 2 and 6 positions of the 4-hydroxybenzyl groups has a hydrogen atom thereon.

36. A compound of claim 34 wherein the hydrocarbyl substituents in the 3 and 5 positions of the 4-hydroxybenzyl groups are alkyl groups.

37. A compound of claim 36 wherein at least one of the alkyl groups in the 3 and 5 positions of the 4-hydroxybenzyl groups is a secondary or tertiary alkyl group.

38. A compound of claim 36 wherein both of the alkyl groups in the 3 and 5 positions of the 4-hydroxybenzyl groups are secondary or tertiary alkyl groups.

39. A compound of claim 36 wherein one of the alkyl groups in the 3 or 5 positions of the 4-hydroxybenzyl groups is a primary alkyl group and the other such alkyl group is a secondary or tertiary alkyl group.

40. A compound of claim 36 wherein one of the alkyl groups in the 3 or 5 positions of the 4-hydroxybenzyl groups is a methyl group and the other such alkyl group is a tertiary alkyl group.

41. A compound of claim 40 wherein the tertiary alkyl group is a tertiary butyl group.

42. A compound of claim 36 wherein both of the alkyl groups in the 3 and 5 positions of the 4-hydroxybenzyl groups are tertiary alkyl groups.

43. A compound of claim 42 wherein the tertiary alkyl groups are tertiary butyl groups.

44. 4-(1,3-hexahydropyrimidinylmethylene)-2,6-di-tert-butylphenol, a compound of claim 1.

45. 4,4'[1,3-hexahydropyrimidinediylbis(methylene)]-bis-(2,6-di-tert-butylphenol), a compound of claim 1.

46. A process for producing hexahydropyrimidine compounds which comprises reacting formaldehyde and 1,3-propanediamine with (i) at least one phenol having a hydrogen atom in the 6-position and having positions 2 and 4 wherein at least each of the 2- and 4-positions are substituted such that said substituted 2 and 4 positions do not interfere with said process, or (ii) at least one phenol having a hydrogen atom in the 4-position and having positions 2 and 6 wherein at least each of the 2- and 6-positions are substituted such that said substituted 2 and 6 positions do not interfere with said process, or (iii) a mixture of at least one phenol having a hydrogen atom in the 6-position and having positions 2 and 4 wherein at least each of the 2- and 4-positions are substituted such that said substituted 2 and 4 positions do not interfere with said process, and at least one phenol having a hydrogen atom in the 4-position and having positions 2 and 6 wherein at least each of the 2- and 6- positions are substituted such that said substituted 2 and 6 positions do not interfere with said process, such that at least one hyxahydropyrimidine compound is formed.

47. A process as claimed in claim 46 wherein said substituted 2- and 4- positions and said substituted 2- and 6-positions contain a hydrocarbyl group.

48. A process as claimed in claim 46 wherein the formaldehyde and 1,3-propanediamine are reacted with a 2,6-dialkylphenol.

49. A process as claimed in claim 46 wherein the formaldehyde and 1,3-propanediamine are reacted with 2,6-di-tert-butylphenol.

* * * * *

UNITED STATES PATENT AND TRADEMARK OFFICE
CERTIFICATE OF CORRECTION

PATENT NO. : 5,106,975
DATED : APRIL 21, 1992
INVENTOR(S) : DENNIS J. MALFER, ET AL.

It is certified that error appears in the above-identified patent and that said Letters Patent is hereby corrected as shown below:

Col. 14, Line 50, change "butyl" to
-- alkyl --

Signed and Sealed this

Twentieth Day of July, 1993

Attest:

MICHAEL K. KIRK

*Attesting Officer*     Acting Commissioner of Patents and Trademarks